United States Patent [19]
Crueger et al.

[11] Patent Number: 5,989,882
[45] Date of Patent: Nov. 23, 1999

[54] PROCESSES FOR PREPARING ACARVIOSYL TRANSFERASE AND FOR USING IT IN THE CONVERSION OF ACARBOSE HOMOLOGUES INTO ACARBOSE, FOR THE PREPARATION OF ACARBOSE HOMOLOGUES

[75] Inventors: Anneliese Crueger, Erkrath; Hans-Georg Dellweg, Wuppertal; Jürgen Georg Lenz, Leverkusen; Werner Schröder, Wuppertal; Hermann Pape, Münster; Klaus Goeke, Menden; Beate Schaper; Michael Hemker, both of Münster; Wolfgang Piepersberg; Jürgen Distler, both of Wuppertal; Ansgar Stratmann, Hattingen, all of Germany

[73] Assignee: Bayer Aktiengesellschaft, Leverkusen, Germany

[21] Appl. No.: 08/816,105

[22] Filed: Mar. 14, 1997

[30] Foreign Application Priority Data

Mar. 22, 1996 [DE] Germany ............................ 196 11 252
Jun. 25, 1996 [DE] Germany ............................ 196 25 269

[51] Int. Cl.$^6$ .............................. C12N 9/10; C12N 15/00; C12N 1/20; C07H 21/04
[52] U.S. Cl. ................. 435/193; 435/252.3; 435/254.11; 435/320.1; 435/325; 435/410; 536/23.2
[58] Field of Search ................................. 435/193, 320.1, 435/252.3, 254.11, 325, 410; 536/23.2; 935/22

[56] References Cited

U.S. PATENT DOCUMENTS

| | | | |
|---|---|---|---|
| 3,937,817 | 2/1976 | Frommer et al. | 424/115 |
| 3,951,745 | 4/1976 | Frommer et al. | 195/80 R |
| 4,062,950 | 12/1977 | Frommer et al. | 424/181 |

FOREIGN PATENT DOCUMENTS

| | | |
|---|---|---|
| 0 730 029 | 9/1996 | European Pat. Off. . |
| 20 64 092 | 7/1972 | Germany . |
| 22 09 834 | 9/1973 | Germany . |
| 23 47 782 | 4/1975 | Germany . |
| 195 07 214 | 10/1996 | Germany . |
| WO 97/47748 | 12/1997 | WIPO . |
| WO 98/38313 | 9/1998 | WIPO . |

OTHER PUBLICATIONS

Rudinger (1976) Characteristics of the amino acids as components of a peptide hormone sequence. In: Peptide Hormones. Ed. J. A. Parsons. University Park Press, Baltimore, MD. pp. 1–7, Jun. 1976.
Ngo et al. (1994) Computational complexity, protein structure prediction, and the ILevinthal paradox. In: The Protein Folding Problem and Tertiary Structure Prediction. Eds. Merz et al. Birkhauser et al. Boston, MA. pp. 491–495 Jan. 1994.
Thornton et al. (1995) Protein Engineering: Editorial Overview. Current Opinion in Biotechnology 6(4): 367–369, Aug. 1995.
Wallace (1993) Understanding cytochrome c function: engineering protein structure by semisynthesis. The FASEB Journal 7: 505–515, Apr. 1993.
Schaper, Beat: "Biochemische und Physiologische Studien zur Biosynthese des Alpha–Glucosidase–Inhibitors Acarbose" pp. 73 –115 (1991).
Lanson et al., "Nucleotide Sequence and X–Ray Structure of Cyclodextrin Glycosyltransferase from *Bacillus Circulans* Strain 251 in a Maltose–dependent Crystal Form" Journal of Molecular Biology, pp. 590–600 (1994).
Bibb, et al. (1994) Mol. Microbiol. 14, pp. 533–545.
Birnboim, J. Doly (1979) Nucleic Acids Res. 7, pp. 1513–1523.
Hanahan (1983) J. Mol. Biol. 166, pp. 557–580.
Hopwood, et al. (1985) Genetic manipulation of Streptomyces; A laboratory manual; The John Innes Foundation, Norwich, England.
Ingham, et al. (1995) Nucleic Acids Res. vol. 23, pp. 370–373.
Lugtenberg, et al. (1975), FEBS Lett., vol. 58, pp. 254–258.
Madon, Hütter (1991), J. Bacteriol., vol. 173, pp. 6325–6331.
Mazodier, et al. (1989), J. Bacteriol. vol. 171, pp. 3583–3585.
Sanger, et al. (1977), Proc. Natl. Acad. Sci, USA 74, 5463–5467.
Southern, (1975), J. Mol. Biol. 98, 503–521.
Wehmeier, (1995), Gene 165, pp. 149–150.
Goeke, (1986), Enzymatische Untersuchungen zum Zuckerstoffwechsel und zur Biosynthese des α–Glucosidase–Inhibitors Acarbose bei Actinoplanes spec.; Dissertation Uni Münster.
Schaper (1991), Biochemische und physiologische Studien zur Biosynthese des α–Glucosidase–Inhibitors Acarbose; Dissertation Uni Münster.
User's manual protein sequencing system model 473A (1989), Applied Biosystems Foster City, CA 94404, USA.

*Primary Examiner*—Bradley L. Sisson
*Assistant Examiner*—Einar Stole
*Attorney, Agent, or Firm*—Sprung Kramer Schaefer & Briscoe

[57] ABSTRACT

The invention relates to acarviosyl transferase from actinomycetes, mainly from Actinoplanes sp. SE 50/110 and its mutants, to a process for isolating, purifying and characterizing the enzyme, to the isolation and characterization of the acbD gene encoding the acarviosyl transferase, to the expression of the acarviosyl transferase in a heterologous host organism, to the use of the acarviosyl transferase for converting acarbose minor constituents into acarbose or for preparing acarbose homologues, to the use of the acarviosyl transferase in acarbose purification, and also to the preparation of production mutants in which formation of minor constituents is reduced by means of inactivation of the acarviosyl transferase gene.

9 Claims, 4 Drawing Sheets

Structure of the expression vector pUWL201
(U. Wehmeier, not published)

Fig. 3

Protein sequence    725 a.a.   VQRHARHAIAAA ... GTGTTSLTWQRZ

```
        |   10     |   20     |   30     |   40     |   50     |   60
  1 VQRHARHAIA AAVGFPLLPP SLPAHAAGAS AVVPYAGNPA SLKQDLCYQI ATDRFSDGTP  60
 61 ANNNPGNVPG MFADKTKLND RQEWLKYMGG DFAGITQRME YLKNLGVGAI WISPHVDNIN 120
121 VPANGATGYH GYWPRDFKRL EEHFGTDEEF DALVSAAHAS NIKVIMDWTP NGTNPPNQAE 180
181 DGALYDDGQL VGRYGADSAG HFHHGPAIGD FNDRYQDQYY SLADIADLDQ QNPRVDQLLK 240
241 DDANYWMDRG VDGIRVDAVK HMPLSWQRSF ADAVTSHKSA AIFGEWYMGD QSDPLYADQV 300
301 KFANTSGIAA MDFYTNRSIR DTFAGAGSMK SLDAAITKTN RDYLYEQDLI TFLDNQDTRR 360
361 FGTLNSDPAA LHRALAFLLT TRGTPCLFYG TEQYLHNDTG EGSNKGKDPY NRPPMASFDT 420
421 DTVAYREIRR PLRPAPVEPR GGYGDHQQRW INDDVYVYER RFGDNVLLTA INKGSHEYRL 480
481 ERAGTALPAG TYRDVLGGTF GGSDLTVEDG DGTDRSTVAP VLGAGQVAVW SYRAPVDTEP 540
541 RIGGVGPVVT RAGATVTVEG TGFGSGGTVA IGGVPATVQQ WTADRITATV PVGVPTGAVQ 600
601 VTVGNGSGTS NGYPITTRTG KPVPVQFTVQ NPPATAPGES LYLTGDVAEL GHWSTSPDQT 660
661 AGQLLRVPNE SRGVLVADLP AGAPVEFKFV KVAADGTVTW EGGANHRYTV PAGGTGTTSL 720
721 TWQRZ                                                             725
        |   10     |   20     |   30     |   40     |   50     |   60
```

Fig. 4

DNA sequence 2582 b.p. AAGCTTgaaGTG...CTGCTTCTGCAG linear

```
          |   10       |   20       |   30       |   40       |   50       |   60
    1 AAGCTTgaaG TGGCGGTGAT GCATCCATCA CTGTATGCGC ATCTGAATGA CGTCTTCTGC   60
   61 AAGTTCTTGC AGCGGTCTCC GGGCCCTGCC CTTCCTCGTC ATCCCTTCAC AAGGAGAAGC  120
  121 TCGTGCAACG TCACGCCAGG CATGCCATCG CCGCGGcGGT AGgcTTTccG CTGCTGCCGC  180
  181 CGTCACTGCC GGCTCATGCC GCCGGGGCTT CGGCCGTGGT GCCGTACgCC GGTAACCCGG  240
  241 CCAGTCTCAA GCAGGACCTC TGCTACCAGA TCGCCACCGA CCGGTTCAGC GACGGGAcCC  300
  301 cggCGAaCAa CAaTCCGGGC AACGTGCCCG gCATGTTCGC CGACAAGACC AAGCTGAACG  360
  361 ACCGGCAGgA GTGGCTCAAA TACATGGGAG GTGACTTCGC CGGCATCACC CAGCGGATGG  420
  421 AGTACCTCAA GAACCTGGGC GTCGGcgCGA TCTGGAtctc gCCGCACGTC GACAACATCA  480
  481 ACGTTCCGGC GAACGGCGCC ACCGGTTACC ACGGCTACTG GCCGCGCGAC TTCAAGCGGC  540
  541 TCGAAGAGCA CTTCGGCACC GACGAGGAGT TCGACGCGCT GGTGTCGGCG GCGCACGCCA  600
  601 GCAACATCAA AGTGATCATG GACTGGACGC CGAACGGCAC CAACCCGCCG AACCAGGCCG  660
  661 AGGACGGCGC CCTcTACGAC GATGGGCAGC TGGTCGGCAG GTACGGGgcg GACAGTGCCG  720
  721 GGCAcTTCCA CCACGGCCCG GCGATCGGCG AcTTCAACGA TCGcTACCAG GACCAgTAcT  780
  781 ACAGcCTGgC CGAcATCGCC GAcCTCGACC AGcagaaccc gcgggtcgac cagCTGCTCA  840
  841 AGGACGACGC CAACTACTGG ATGGACCGCG GGGTCGACGG CATCCGGGTC GACGCCGTCA  900
  901 AGCACATGCC GCTGAGCTGG CAGCGGTCCT TCGCCGACGC GGTCACCTCG CACAAGAGCG  960
  961 CGGCCATCTT CGGCGAGTGG TACATGGGCG ACCAGTCCGA TCCGCTCTAC GCCGACCAGG 1020
 1021 TCAAGTTCGC CAACACCAGC GGCATCGCGG CCATGGACTT CTACACCAAC CGCTCGATCC 1080
 1081 GCGACACCTT CGCCGGCGCC GGCTCGATGA AGTCCCTGGA CGCGGCGATC ACCAAGACCA 1140
 1141 ACCGGGACTA CCTCTACGAG CAGGATCTGA TCACGTTCCT GGACAACCAG GACACCCGGC 1200
 1201 GCTTCGGGAC GCTCAACAGC GATCCGGCGG CCCTGCACCG GCGCTCGCC TTCCTGCTCA 1260
 1261 CCACCCGGGG TACGCCGTGC CTGTTCTACG GCACCGAGCA GTACCTGCAC AACGACACCG 1320
 1321 GTGAGGGCAG CAACAAGGGC AAGGACCCGT ACAACCGGCC CCCGATGGCC AGTTTCGACA 1380
 1381 CCGACACGGT CGCCTACCGG GAGATcCGGC GCCCTCTCCG ACCTGCGCCG GTCGAACCCC 1440
 1441 GCGGTGGCTA CGGGGACCAC CAGCAGCGGT GGATCAACGA CGACGTGTAC GTCTACGAGC 1500
 1501 gCcGGTTCGG CGACAACGTG CTGCTGACCG CCATCAACAA GGGCTCGCAC GAGTACCGGC 1560
 1561 TCGAACGGGC TGGCACCGCG CTGCCGGCCG GCACCTATCG CGACGTGCTC GGCGGCACcT 1620
 1621 TCGGCGGCTC CGACCTGACC GTCGAGGACG GCGACGGCAC CGACCGGTCG ACCGTCGCGC 1680
 1681 CGGTGCTGGG TGCCGGGCAG GTCGCCGTCT GGTCGTACCG GGCGCCGGTG GACACCGAGC 1740
 1741 CCCGGATCGG CGGGGTCGGG CCGGTCGTGA CCCGGGCCGG CGCCACCGTC ACCGTCGAGG 1800
 1801 GCACCGGCTT CGGCTCCGGC GGAACCGTCG CGATCGGCGG AGTCCCCGCG ACCGTCCAGC 1860
 1861 AGTGGACGGC GGACCGTATC ACCGCCAcCG TCCCGGTCGG CGTTCCCACC GGGGCCGTCC 1920
 1921 AGGTGACCGT CGGCAACGGC TCCGGCACCA GCAACGgGTA CCCGATCACC ACcCGTACCG 1980
 1981 GAAAACCGGT CCCGGTGCAG TTCACCGTTC AGAACCCGCC GGCCACCGCG CCCGGGGAGT 2040
 2041 CGCTCTACCT GACCGGTGAC GTCGCCGAGT GGGGCACTG GTCGACCAGC CCGGACCAGA 2100
 2101 CCGCGGGACA GCTGCTGCGG GTGCCGAACG AGTCCCGGGG CGTCCTCGTC GCCGACCTGC 2160
 2161 CGGCCGGGGC GCCGGTCGAG TTCAAGTTCG TCAAGGTCGC GGCCGACGGC ACGGTGACCT 2220
 2221 GGGAGGGTGG TGCCAAcCAC cGGTACACCG TCCCGGccGG CGGCACCGGc ACGACCAGcC 2280
 2281 TCACCTGGCA GcGCTGACGC CACCGTGcGG AGGgCCCGGC CGTGACCGGG CCCGCCGCAC 2340
 2341 CGGGCCGGGC GgTGGAACGG CCGGGACGGT TGGCGCCGG CCCCGGcGTG CGCAgATCGA 2400
 2401 GGGcTGCGCA CACCGGGGGC TTGAACGGCT GGTCTGGCCC CaAGgcGaCG GtTCCCGTCG 2460
 2461 GCGAGTATCT CACCTTCAAG GGTCCCCGGA CGCCTCGCCC GGCTTCTCCA CCAGCGCCGA 2520
 2521 CGGTTACCAG ATCACCCCTT GGTGGAGCCG AGGGAGAGGC CGGCGATGAA CTGCTTCTGC 2580
 2581 AG                                                              2582
          |   10       |   20       |   30       |   40       |   50       |   60
```

PROCESSES FOR PREPARING ACARVIOSYL TRANSFERASE AND FOR USING IT IN THE CONVERSION OF ACARBOSE HOMOLOGUES INTO ACARBOSE, FOR THE PREPARATION OF ACARBOSE HOMOLOGUES

The invention relates to acarviosyl transferase (AT) from actinomycetes, mainly from Actinoplanes sp. SE 50/13 or SE 50/110 and its mutants, to a process for isolating, purifying and characterizing the enzyme, to the isolation and characterization of the acbD gene encoding the acarviosyl transferase, to the expression of acarviosyl transferase in a heterologous host organism, to the use of acarviosyl transferase for converting acarbose minor constituents into acarbose or for preparing acarbose homologues, to the use of acarviosyl transferase in acarbose purification and to the preparation of production mutants in which formation of minor constituents is reduced by means of inactivating the acarviosyl transferase.

The discovery that a series of actinomycetes, especially the Actinoplanaceae, form oligosaccharide-like inhibitors of glycoside hydrolases, primarily carbohydrate-cleaving enzymes of the digestive tract, is the subject-matter of previous patent applications (e.g. DE 20 64 092 and DE 22 09 834). The inhibitors consist of an acarviosyl unit which is linked α-1,4-glycosidically to maltooligosaccharides or other sugars. The acarviosyl core can be linked on both sides to differing numbers of glucose units. The number of glucose residues on the core determines the specific activity of the inhibitor. Relatively short molecules (components containing 1–5 glucose units) act mainly on disaccharidases, whereas the effect on α-amylases becomes more efficient as the number of glucopyranoses increases. As the most potent α-glucosidase inhibitor of this group, the compound O-4,6-dideoxy-4-[[1S-(1S,4R,5S,6S)-4,5,6-trihydroxy-3-(hydroxymethyl)-2-cyclohexen-1-yl]-amino]-D-glucopyranosyl-(14)-O-D-glycopyranosyl-(14)-D-glucopyranose is described as acarbose [DE 23 47 782].

Acarbose is employed in human medicine in the control of diabetes mellitus. The secondary metabolite acarbose is formed by Actinoplanes sp. SE 50 (CBS No. 961.70) and by a natural variant of this strain, SE 50/110 (CBS 674.73), or else by SE 50/13 (CBS 614.71) [DE 22 09 83] and by their selectants and mutants. The isolation of a saccharase inhibitor of this nature is described in the patent applications mentioned, for example in Examples 1 to 4 of the said German Patent Application P 20 09 834. In association with this isolation, acarviosyl-containing compounds possessing differing numbers of maltooligosaccharide and disaccharide residues appear as minor constituents in addition to acarbose as the main product.

Acarbose consists of an acarviosyl residue which, according to the current state of knowledge, is formed first during the biosynthesis in order then to be linked to a maltosyl residue. In 1986, during the course of studies designed to elucidate the biosynthesis of acarbose, Goeke (Goeke, K., Enzymatische Untersuchungen zum Zuckerstoffwechsel und zur Biosynthese des α-Glucosidase-Inhibitors Acarbose bei Actinoplanes spec. [Enzymic investigations on sugar metabolism and on the biosynthesis of the α-glucosidase inhibitor acarbose in Actinoplanes spec.]; Dissertation, Münster University) described an enzymic exchange of the maltosyl residue of the acarbose (acarviosyl-maltose) for a radioactively labelled maltose: when [U-$^{14}$C]-maltose is used, an acarbose is formed which is radioactively labelled in the maltosyl residue. The enzyme involved, i.e. acarviosyl transferase (AT), was initially termed pseudodisaccharidyl(PDS) transferase. From the fact that the activity of the pellet fraction, following cell disruption and differential centrifugation, was greater by a factor of 3.25 than the acarbose/maltose exchange reaction of the supernatant fraction, it was concluded that the PDS transferase was membrane-bound. In 1991, Schaper (Schaper, B., Biochemische und physiologische Studien zur Biosynthese des α-Glucosidase-Inhibitors Acarbose [Biochemical and physiological studies on the biosynthesis of the α-glucosidase inhibitor acarbose]; Dissertation, Münster University) confirmed this finding and elaborated a detailed working-up procedure for the membrane-bound enzyme. A pH optimum of 4.5 was cited for the partially purified enzyme, at a temperature optimum of 30° C. and using $Mn^{2+}$ as a cofactor.

It has now been found, surprisingly, that the acarviosyl transferase which possesses the ability to exchange the maltosyl residue of acarbose is not present in membrane-bound form; on the contrary, the AT is mainly present in the culture filtrate, with the enzyme activity increasing in parallel with cell growth. It was possible to isolate the enzyme at high purity from the cell supernatant. For this purpose, the enzyme was precipitated from the culture supernatant using ammonium sulphate. After centrifugation, the sediment was dissolved in buffer (containing glycerol and $CaCl_2$), after which this solution was centrifuged once again and the resulting supernatant was passed through an anion exchange column. The run-through contained the acarviosyl transferase. The AT was obtained from this solution by dialysis as a partially enriched preparation, or else purified by chromatography on DEAE-Fractogel®, precipitating twice with sedimentable starch and desorbing with acarbose or maltose.

The purified acarviosyl transferase has a MW of 76 kDa (SDS-PAGE) and a temperature optimum of 20–40° C. The enzyme is temperature-stable up to approx. 40° C. A pH optimum of 6.2–6.9 was determined, as was a dependency on $Ca^{2+}$ ions.

The purified enzyme was sequenced. Surprisingly, the resulting base sequence exhibits good agreement with the corresponding DNA sequence of the acbD gene from the acarbose gene cluster of the producing organism Actinoplanes sp. SE 50/110.

It is furthermore surprising that acarviosyl transferase can replace the maltosyl residue of acarbose with other sugar residues, with the formation of acarbose homologues, or is able to form acarbose by replacing the sugar residues of the acarbose-like minor constituents, which are formed during the fermentation, with a maltose residue. In this context, acarviosyl transferase is catalyzing the general reaction

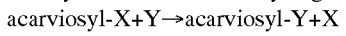

acarviosyl-X+Y→acarviosyl-Y+X (X=glucose, maltose, maltooligosaccharides and other sugars, Y=glucose, maltose, maltooligosaccharides and other sugars).

The invention therefore discloses:

The complete process for isolating and purifying acarviosyl transferase from cultures of Actinoplanes sp. SE 50/110 or its mutants.

The characterization of the purified acarviosyl transferase.

The amino acid sequence which was determined over more than 100 amino acids following tryptic cleavage of the enzyme. The base sequence which is obtained from this amino acid sequence exhibits good agreement with the base sequence of the acbD gene.

A process for preparing acarbose from acarbose minor constituents by replacing the respective sugar residues with maltose.

A process for preparing acarbose homologues possessing altered pharmacological properties by means of replacing the maltosyl residue of acarbose with other suitable sugar residues.

The use of acarviosyl transferase, or immobilized AT, for isolating acarbose from the culture broth (affinity chromatography) while at the same time converting acarbose homologues into acarbose.

The isolation and characterization of the acbD gene encoding acarviosyl transferase.

The recombinant preparation of acarviosyl transferase in an heterologous host organism.

The preparation of improved production mutants, with the product spectrum in Actinoplanes being restricted to acarbose, as the desired main product of the biosynthesis, by means of switching off the unwanted formation of minor constituents by inactivating the acbD gene.

The invention is described in detail below. The invention is furthermore determined by the content of the claims.

The invention is described in detail below.

BRIEF DESCRIPTION OF THE DRAWINGS

FIG. 3 Protein sequence (SEQ ID NO: 1).

FIG. 4 Nucleotide Sequence (SEQ ID NO: 2).

I. Enzyme purification

Figure 1:
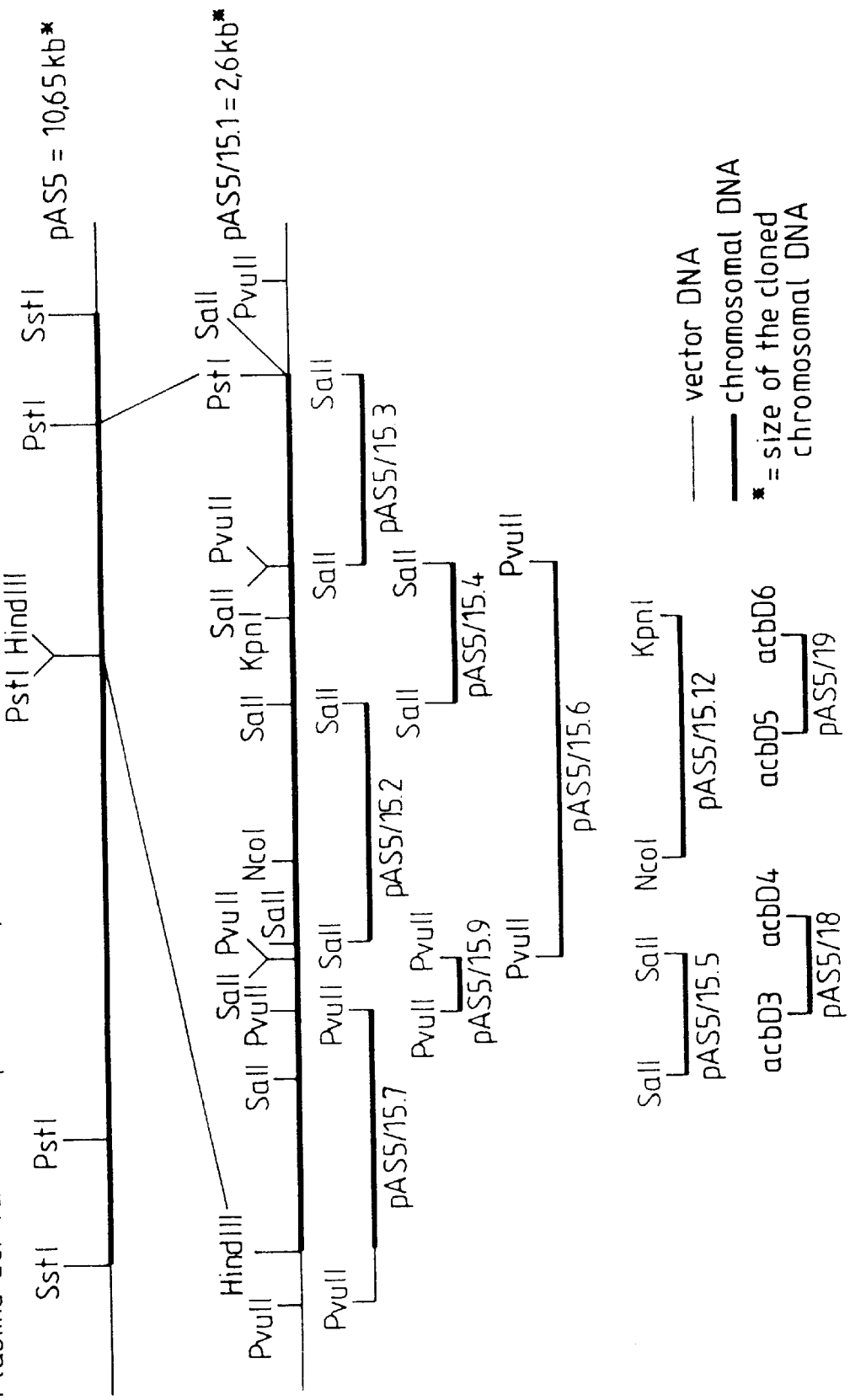
FIG. 1 Plasmid derivatives of pAS5 pAS5/15.1 for DNA sequencing.

Culture filtrate from the two-phase growth of Actinoplanes sp. SE 50/110 or its mutants:

| Seed culture: | soya bean meal, defatted | 2% |
|---|---|---|
| | glycerol | 2% |
| | CaCO₃ | 0.2% |
| | tap water | |
| | pH 7.2, adjusted using NaOH | |
| | 1000 ml Erlenmeyer flask, filled to a volume of 125 ml | |
| | inoculum: 5 ml of stock culture (72 h seed culture, storage at 20° C.) | |
| | incubation: 72 h at 30° C. and 260 rpm | |
| Main culture: | soya bean meal, defatted | 1% |
| | starch | 3% |
| | CaCO₃ | 0.2% |
| | tap water | |
| | 1000 ml Erlenmeyer flask, filled to a volume of 125 ml | |
| | inoculum: 5 ml of seed culture | |
| | incubation: 96–144 h at 30° C. and 260 rpm. | |

The maximum AT activity, of 2.6 nkat/ml of culture filtrate, is reached after a culturing period of 120 h. AT is then the quantitatively predominant protein in the culture filtrate.

The purification scheme is depicted in Table 1.

TABLE 1

Scheme for purifying acarviosyl transferase

The following buffers were used:

Buffer 1: 25 mM Tris/HCl pH 8.5+10% glycerol +1 mM CaCl$_2$

Buffer 2: 25 mM Tris/HCl pH 7.5+1 mM CaCl$_2$

Buffer 3: 10 mM Tris/HCl pH 7.5+1 mM CaCl$_2$

Buffer 4: 0.1 mM Tris/HCl pH 7.2+0.01 mM CaCl$_2$

Starch*: boiled, soluble starch, 12 h at 4° C. ("cold precipitation"), centrifugation at 40,000×g for 60 min; the sediment is employed.

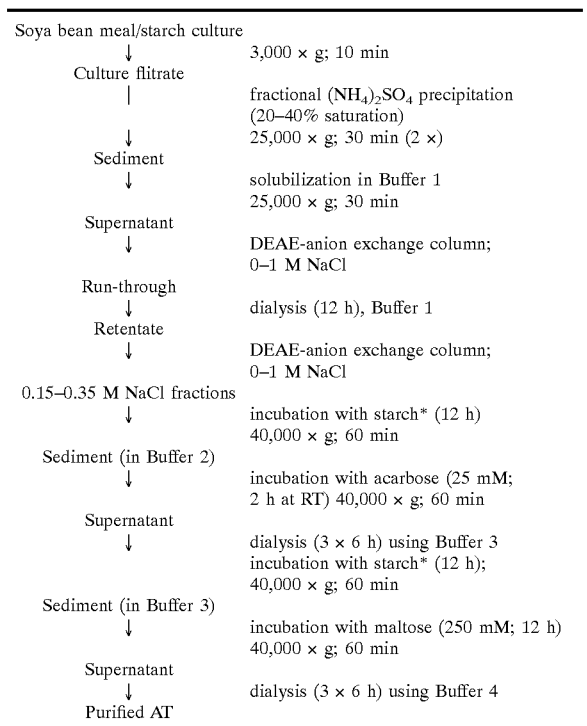

The purification is summarized in Table 2

TABLE 2

Purification of acarviosyl transferase, summary (for the sample designation, see the purification scheme in Tab. 1)

| Purification step | Total protein (mg) | Total activity (nkat) | spec. activity (nkat/mg) | Yield (%) | Enrichment |
|---|---|---|---|---|---|
| Culture filtrate | 400 | 1740 | 4.35 | 100 | 1 |
| 20–40% (NH₄)₂SO₄ | 139 | 1147 | 7.75 | 66 | 1.8 |
| Run-through 1st column | 89 | 1078 | 12.1 | 62 | 2.8 |
| Active fraction 2nd column | 20 | 789 | 38.8 (43.1)* | 45 | 8.9 |
| Starch precipitation + acarbose desorption | 9.7 | 538 | 55.5 | 31 | 12.8 |
| Starch precipitation + maltose desorption | 5.5 | 425 | 77.3 | 24 | 17.8 |

*most active fraction

The purification of the AT results in a 17.8-fold enrichment with a yield of 24%.

II. Determination of acarviosyl transferase activity

1. Radioactivity test a) Acarbose or acarbose homologues were incubated at 30° C. with [$^{14}$C]-maltose in a tris-maleate buffer (pH 6.3) in the presence of preparations containing acarviosyl transferase. The acarbose was then separated from the maltose using a cation exchange resin. The level of [$^{14}$C] radioactivity in the acarbose fraction in relation to the total radioactivity gives the replacement rate, which is correlated with the AT activity.

Acarviosyl-(α-1,4)-(sugar)+[$^{14}$C]-maltose→acarviosyl-(α-1,4)-[$^{14}$C]-maltose+sugar b) [$^{14}$C]-Acarbose (labelled in the maltose unit) was incubated together with maltooligosaccharides or other sugars in the presence of AT, as in a). The mixture was treated and evaluated as described in a).

Acarviosyl-(α-1,4)-[$^{14}$C]-maltose+sugar→acarviosyl-sugar+[$^{14}$C]-maltose

2. Thin layer chromatography

Acarbose or acarbose homologues were incubated with maltose, maltooligosaccharides or other sugars, as described in a). The reaction mixture contained:

10 μl of AT preparation (AT in 0.1 mM Tris/HCl pH 7.2+0.01 mM CaCl$_2$; 4.5 nkat/ml)

10 μl of acarbose (70 mM stock solution) or acarbose homologues (approx. 30 mM)

10 μl of substrate (70 mM stock solution) or maltose (600 mM)

Sample preparation

30 μl of reaction mixture
↓ 18 h; 30° C.
addition of 70 μl of ethanol
↓ centrifugation for 5 min at 7000 g removal of 80 μl of supernatant→5 μl for the TLC
↓
75 μl
↓ drying in a vacuum concentrator
sample for HPLC TLC: silica gel 60 TLC aluminium foils (Merck), mobile phase: butanol: ethanol: water (50:30:20); staining: Cer spray reagent; development at 110° C.

3. HPLC Test

Acarbose or acarbose homologues were incubated with maltose, maltooligosaccharides or other sugars as described in 2. After precipitating the proteins, the chemical composition of the remaining solution was analyzed by means of ECD HPLC or UV HPLC.

III. Properties of acarviosyl transferase

| | |
|---|---|
| Molar mass | 76 kDa (SDS-PAGE) |
| pH optimum | 6.2–6.9 |
| Temperature optimum | 30° C. (20–40° C.) |
| Temperature stability | up to approx. 40° C. |
| Trace element dependence | Ca$^{2+}$ |

The following general formula for the acceptor molecule can be deduced on the basis of the acceptor speficities which are listed below.

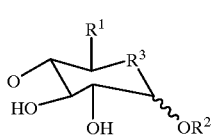

R$^1$ is H, CH$_2$OH or CH$_3$
R$^2$ is H, (CH$_2$)$_m$CH$_3$, m=0–10
  pyranoses [α(1→2), (1→3), (1→4), (1→6), β(1→2), (1→3), (1→4)]
  furanoses [α(1→6)]
  glucitol, phenyl-, nitrophenyl-, etc.
R$^3$ is O, S or CHOH Acceptor specificity
cellobiose
deoxy-D-glucose
D-gluconic acid lactone
D-glucose
isomaltose
isomaltotriose
laminaribiose (3-O-β-D-glucopyranosyl-D-glucose)
maltose
maltotriose
maltotetraose
maltopentaose
maltohexaose
maltoheptaose
methyl-D-glucopyranoside
palatinose
panose (6-α-glycosyl-maltose)
sophorose (2-O-β-D-glucopyranosyl-α-D-glucose)
xylobiose
L-xylose
D-xylose
nigerose
L(-)-glucose
5-thio-D-glucose
myo-inositol
maltitol
amygdalin
amylopectin
dextrin
α-D(+)-maltose-1-phosphate
4-nitrophenyl-α-D-glucopyranoside
4-nitrophenyl-β-D-xylopyranoside
D(-)-salicin
phenyl-α-D-glucopyranoside
octyl-D-glucopyranoside
nonyl-β-D-glucopyranoside
octyl-β-D-maltopyranoside
decyl-β-D-maltopyranoside Donor specificity
acarbose
acarbose minor constituent 2
acarbose minor constituent 4A
acarbose minor constituent 4B
acarbose minor constituent 4C
acarbose minor constituent B
pseudoacarbose IV. Protein sequencing The N-terminal sequences of fragments of acarviosyl transferase were analyzed using an Applied Biosystems 473A gas-liquid solid-phase protein sequencer (Foster City, Calif., U.S.A.). The standard sequencing programme for this equipment was used. The appliance, the programmes which are used and the PTH separation system are described in detail in the user's manual (user's manual protein sequencing system model 473A (1989), Applied Biosystems, Foster City, Calif. 94404, U.S.A.).

The PTH amino acids were detected on-line using an Applied Biosystems RP-18 column (220 mm×2 mm, 5μ material). Identification and quantitative determination of the PTH amino acids were effected with the aid of a 50 pM standard of all the PTH amino acids. The Applied Biosystems Sequencer Data System 610A was used for evaluating the data. The chemicals which were used for the protein sequencer were obtained from Applied Biosystems.

The Pharmacia (Freiburg, Germany) Smart System was employed for separating the tryptic peptides.

The HPLC column (2.1 mm×100 mm; 5μ material) for separating the tryptic peptides was obtained from Pharmacia (Freiburg, Germany), while trypsin (sequence grade) was obtained from Boehringer Mannheim and all the remaining chemicals were obtained from Merck (Darmstadt, Germany) or Sigma (Deisenhofen, Germany).

V. Isolation and sequencing of the acbD gene (AcbD protein=AT)

Unless otherwise indicated, all the genetic manipulation methods were carried out as described in Sambrook et al. (Molecular Cloning; A laboratory manual; 2nd edition, 1989; Cold Spring Harbour Laboratory Press, N.Y., U.S.A.).

The gene probe which was used for the screening was isolated from the plasmid pAS2 (DE 195 07 214). Plasmid pAS2 was prepared from *E. coli* DH5α by means of the boiling method or by alkaline lysis and hydrolyzed with the restriction endonuclease BamHI. The resulting 2.2 kb BamHI fragment was isolated and radioactively labelled with $^{32}$P-labelled deoxynucleotides by means of nick translation. This labelled fragment was employed as a gene probe for isolating acarbose biosynthesis genes (DE 195 07 214) and is termed acb probe II in that which follows.

Acarbose biosynthesis genes were isolated as follows. Chromosomal DNA from Actinoplanes sp. SE 50/110 was hydrolyzed with the restriction enzyme SstI, separated by gel chromatography and examined by means of Southern Hybridization, using the acb probe II, for the presence of an homologous DNA sequence. The SstI fragment which was hybridized by the gene probe had a size of 11 kb. The 11 kb SstI fragment was eluted from the gel and ligated into the vector pUC18; this recombinant vector was then cloned into *E. coli* DH5α. The resulting plasmid was given the designation pAS5. Plasmid pAS5 was hydrolyzed with the restriction enzymes PstI and HindIII. The resulting fragments had the following sizes:

1.4 kb PstI fragment 5.4 kb PstI fragment 0.05 kb PstI/HindIII fragment 2.6 kb HindIII/PstI fragment 3.8 kb PstI fragment (1.1 kb PstI/SstI fragment ligated to the pUC18 vector)

The 2.6 kb HindIII/PstI fragment was eluted from the gel and ligated into the pUC 18 vector; this recombinant vector was then cloned in *E. coli* DH5α. The resulting plasmid (pAS5/15.1) was hydrolyzed with various restriction endonucleases and the resulting DNA fragments in pUC18 were subcloned in *E. coli* DH5α and sequenced. In order to check the DNA sequences of the fragments derived from pAS5/15.1, DNA fragments were also amplified from Actinoplanes sp. chromosomal DNA by the PCR method, ligated into pUC18, cloned in *E. coli* DH5α and then sequenced. The DNA sequences of the PCR primers were deduced from the DNA sequences of the subcloned fragments from pAS5/15.1 (see below).

For determining the DNA sequence of the 2.6 kb HindIII/PstI fragment from Actinoplanes sp., the following plasmids were constructed and the sequence of the inserted DNA was determined in each case:

| | |
|---|---|
| pAS5/15.1 | = 2.6 kb HindIII/PstI fragment from pAS5 |
| pAS5/15.2 | = 0.75 kb SalI fragment from pAS5/15.1 |
| pAS5/15.3 | = 0.5 kb SalI fragment from pAS5/15.1 |
| pASS/15.4 | = 0.4 kb SalI fragment from pAS5/15.1 |
| pAS5/15.5 | = 0.35 kb SalI fragment from pAS5/15.1 |
| pAS5/15.6 | = 1.25 kb PvuII/fragment from pAS5/15.1 |
| pAS5/15.7 | = 0.7 kb PvuII/HindIII fragment from pAS5/15.1 |
| pAS5/15.9 | = 0.1 kb PvuII fragment from pAS5/15.1 |

-continued

| | |
|---|---|
| pAS5/15.12 | = 0.9 kb KpnI/NcoI fragment from pAS5/15.1 |
| pAS5/18 | = 0.3 kb PCR fragment (primer: see Tab. 3) |
| pAS5/19 | = 0.3 kb PCR fragment (primer: see Tab. 3) |

The method of Sanger et al. (1977), or a method derived from this, was used for the DNA sequencing. The work was carried out using the Autoread Sequencing kit (Pharmacia, Freiburg, Germany) in combination with the Automated Laser Fluorescence (A.L.F.) DNA sequencing appliance (Pharmacia, Freiburg, Germany). Suitable fluorescein-labelled pUC reverse-sequencing and sequencing primers were obtained commercially (Pharmacia, Freiburg, Germany).

TABLE 3

Sequences of the primers for the PCR and the sequencing reaction

Primers for the PCR:

Plasmid pAS5/18:
Primer designation — Sequence

| acbD3 | 5'-ACCAGGCCGAGGACGGCGCCC3' | (SEQ ID NO:3) |
| acbD4 | 5'-AGCGGCATGTGCTTGACGGCG3' | (SEQ ID NO:4) |

Plasmid pAS5/19
Primer designation — Sequence

| acbD5 | 5'-ACCGGCTCGAACGGGCTGGCACC3' | (SEQ ID NO:5) |
| acbD6 | 5'-CCCTCGACGGTGACGGTGGCG3' | (SEQ ID NO:6) |

Primers for the sequencing reaction:

Primer designation — Sequence

| universal printer | 5'GTAAAACGACGGCCAGT3' | (SEQ ID NO:7) |
| reverse primer | 5'GAAACAGCTATGACCATG3' | (SEQ ID NO:8) |

EXAMPLES

1. Preparation, purification and characterization of the acarviosyl transferase

After a seed culture on soya bean meal/glycerol medium, the wild-type strain Actinoplanes sp. 50/110, or a mutant derived from it, was fermented in the production culture on soya bean meal/starch medium at 30° C. on an orbital shaker having a shaking frequency of 260 rpm. Following an incubation which lasted approx. 120 h, the cell mass was separated off. The enzyme was precipitated from the culture supernatant using ammonium sulphate (20–40% saturation). After centrifuging, the sediment was dissolved in buffer (25 mM tris/HCl, pH 8.5, containing a glycerol and $CaCl_2$) and this solution was centrifuged once again. The resulting supernatant was passed through a DEAE anion exchange column. The flow-through contained the acarviosyl transferase. From this solution, the AT was obtained as a partially enriched preparation by means of dialysis or was purified by means of chromatography on DEAE-Fractogel®, precipitating twice with starch and desorbing with acarbose or maltose (see Tab. 1). An enrichment by a factor of 17.8 was achieved in association with a 24% yield.

The activity of the acarviosyl transferase was measured by transferring the acarviosyl residue of acarbose (donor) to maltose (acceptor). The size of the enzyme was determined by SDS-PAGE to be 76,000 Da, with a pH optimum of 6.2–6.9 and a temperature optimum of between 20 and 40° C.

2. Sequencing the acarviosyl transferase

For determining the internal amino acid sequence, the acarviosyl transferase was digested with trypsin. Trypsin cleaves proteins after the amino acids lysine and arginine.

Tryptic cleavage of the AT: Approx. 1 mg of AT was dissolved in 1000 μl of 6M guanidinium chloride/0.5M tris-(hydroxymethyl)-aminomethane, pH 8.6. After adding 30 μl of 1M dithiothreitol (DDT), the sample was reduced at 54° C. overnight. After adding 60 μl of a 2M solution of sodium iodoacetate, the sample was incubated in the dark for 30 min. After that, there followed a dialysis against 0.5M urea/0.1M ammonium hydrogen carbonate (complete buffer exchange after 3 h and overnight; dialysis bag having a 25 kD exclusion). The sample which had been pretreated in this way was digested at 37° C. for 18 h in the presence of 20 μg of trypsin (sequence grade). The sample was concentrated down to approx. 100 μl by drying in a centrifuge.

HPLC separation of the tryptic peptides: One third of the sample was loaded onto an RP-18 column (2.1 mm×100 mm; 5μ material) and separated using a Smart System (solution A: 0.1% TFA, solution B: 0.1% TFA/60% ACN; detection: 215 nm, flow: 0.15 ml/min, room temperature; gradient: 7 min 0% B, 52 min, 70%, 54 min 100% B).

Because of the high molecular weight of the AT, a very complex mixture is formed during the trypsin digestion. Rechromatography of individual fractions is therefore a prerequisite for obtaining clean peptides for the subsequent sequencing.

Rechromatography of separation fractions: The fractions containing the peptides were pooled and concentrated by drying in a centrifuge. The concentrates were rechromatographed on an RP-18 column (2.1 mm×100 mm; 5μ material) (solution A: 0.025M NH$_4$Ac, solution B: 0.025M NH$_4$Ac/60% ACN, pH 6; detection: 215 nm, flow: 0.15 ml/min, room temperature; gradient: 0 min 0% B, 33 min 60%, 38 min 100% B). After rechromatographing fractions 28+29 (Smar 4003) and fraction 30 (Smar 4002) from the first separation using different chromatography conditions, the purity of the resulting peptides was adequate for sequencing the N-terminal sequences.

Sequencing the N-terminal sequences: For example, fraction 32 of the rechromatography (Smar 4002) was evaporated down by drying in a centrifuge. The peptide was dissolved in TFA and, for the sequencing, loaded onto glass fibre filters which had been previously treated with Bio-Brene®. The peptide was sequenced using the "fast-normal" sequencer cycle. The PTH amino acids were identified and determined quantitatively using the 50 pmol PTH standard. The result of the N-terminal sequence analysis is recorded in Tab. 4. A total of 133 amino acids were analyzed from eight tryptic peptides derived from the AT.

TABLE 4

N-terminal sequence of the tryptic peptides derived from acarviosyl transferase 1.1. Rechromatography of fraction 28 + 29 (Smar4003)

1.2. Fraction 35 of the rechromatography

```
1
Asn-Leu-Gly-Val-Gly-Ala-Ile-Trp-Ile-Ser-Pro-His-Val-Asp-Asn-Ile-Asn-Val-Pro-   (SEQ ID NO:9)

22  23
Ala-Ala-Gly-(Gly) . . .
```

2.1 Rechromatography of fraction 30 (Smar4002)

2.2 Fraction 32 of the rechromatography

```
1
Thr-Gly-Lys-Pro-Val-Pro-Val-Gln-Phe-Thr-Val-Gln-Asn-Pro-Pro-Ala-Thr-Ala-Pro-   (SEQ ID NO:10)

21
Gly-Glu . . .
```

2.3 Rechromatography of fraction 25 (Smar4004)

2.3.1 Fraction 31 of the rechromatography

```
1                                                                  18
Ser-Thr-Val-Ala-Pro-Val-Leu-Gly-Ala-Gly-Gln-Val-Ala-Val-Trp-Ser-Tyr-Arg      (SEQ ID NO:11)
```

2.3.2. Fraction 25 + 26 of the rechromatography

```
1
Tyr-Gln-Asp-Gln-Tyr-Tyr-Ser-Leu-Ala-Asp-Ile-Ala-Asp-Leu-Asp-Gln-Gln-Asn-     (SEQ ID NO:12)

20
Pro-(Arg)
```

2.4 Rechromatograpy of fraction 21 (Smar4005)

2.4.1. Fraction 23 of the rechromatography

```
1                                                12
```

TABLE 4-continued

N-terminal sequence of the tryptic peptides derived from acarviosyl transferase Trp-Ile-Asn-Asp-Asp-Val-Tyr-Val-Tyr-Glu-Arg-Leu . . .   (SEQ ID NO:13)

2.5  Rechromatography of fractions 31 + 32 (Smar4001)

2.5.1 Fraction 30 of the rechromatography

```
1                                                      18
Asp-Tyr-Leu-Tyr-Glu-Gln-Asp-Leu-Ile-Thr-Phe-Leu-Asp-Asn-Gln-Asp-Thr-Arg    (SEQ ID NO:14)
```

2.6  Rechromatography of fractions 16 + 17 (Smar4007)

2.6.1 Fraction 17 of the rechromatography

```
1                        9
Asp-Asp-Ala-Asn-Tyr-Trp-Met-Asp-Arg                                        (SEQ ID NO:15)
```

2.7  Rechromatography of fraction 20 (Smar4007)

2.7.1 Fraction 11 of the rechromatography

```
1                                  12
Ala-Val-Leu-Thr-Gly-Asn-Thr-Val-Tyr-Asp-Trp-Lys                            (SEQ ID NO:16)
```

3. Conversion of acarbose homologues into acarbose.

In the investigations on the donor specificity of AT, acarbose homologues, such as the acarbose minor constituents 2, 4A, 4B and 4C and components B and pseudoacarbose

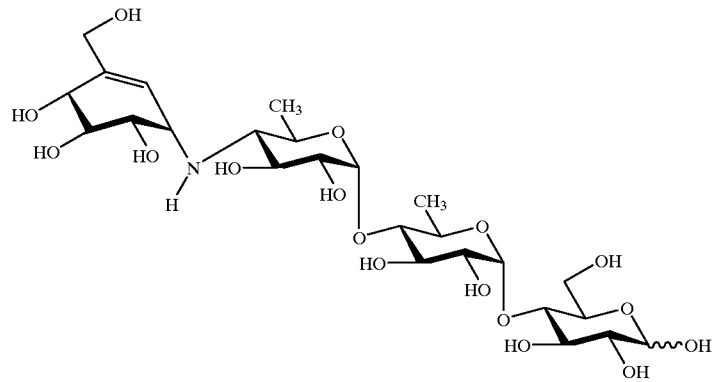

were treated, in experimental mixtures, with maltose in the presence of acarviosyl transferase. After a reaction period of 24 h at 30° C., the experimental mixtures were analyzed by HPLC on amino phase using UV detection. The evaluation (Tab. 5) demonstrates that the content of minor constituents decreases whereas the content of acarbose increases, i.e. there is a transfer of the acarviosyl unit from the acarbose minor constituents 2, 4A, 4B and 4C to maltose.

TABLE 5

The use of AT to convert the acarbose minor constituents 2, 4A, 4B and 4C into acarbose

| | | HPLC analysis (g/l) | | | | |
|---|---|---|---|---|---|---|
| Donors | Reaction | Acarbose | Comp. 2 | Comp. 4A | Comp. 4B | Comp. 4C |
| Comp. 2 Mixture | 0 | 0.29 | 0.60 | | | |
| | 24 | 0.40 | 0.40 | | | |
| Comp. 4A, Comp. 4B, Comp. 4C | 0 | 0.53 | | 0.92 | 0.78 | 0.48 |
| | 24 | 1.70 | | 0.08 | 0.07 | 0.26 |

Traces of a conversion are found with component B and pseudoacarbose.

4. Isolation of higher acarbose homologues from acarbose

In the investigations on the acceptor specificity of AT, acarbose was reacted in experimental mixtures with acarviosyl transferase in the presence of adequately high concentrations of maltooligosaccharides and other sugars. After a reaction period of 18 h at 30° C., the experimental mixtures were analyzed by HPLC on amino phase using UV detection. The evaluation (Tab. 6) demonstrates that newly synthesized saccharides are detected while maltose is concomitantly released.

TABLE 6

Transfer of the acarviosyl residue of acarbose to different sugars acting as acceptors (PA = percentage area; RT = retention time)

| Acceptors | Acarbose | Acceptor | Maltose | New constituents (PA %) | (RT) |
|---|---|---|---|---|---|
| Demin. water | 31.4 | | 2.9 | 0 | |
| Cellobiose | 31.3 | 13.5 | 17.2 | 29 | 25.0 |
| Deoxy-D-glucose | 30.4 | 4.5 | 2.6 | 1 | 6.6 |
| Gluconic acid lactone | 30.6 | 17.1 | 3.7 | 4 | 37.4 |
| D-Glucose | 30.2 | 5.7 | 7.6 | 11 | 18.0 |
| Isomaltose | 31.8 | 10.1 | 9.7 | 16 | 19.6 |
| Isomaltotriose | 30.9 | 13.9 | 5.4 | 7 | 23.5 |
| Laminaribiose | 28.5 | 15.6 | 16.3 | 27 | 30.1 |
| Maltose | 30.2 | 15.8 | 38.1 | | |
| Maltotriose | 31.8 | 26.8 | 19.8 | 21 | 38.8 |
| Maltotetraose | 31.1 | 38.1 | 19.9 | 20 | 40.6 |
| Maltopentaose | 32.6 | 40.6 | 17.9 | 20 | 42.1 |
| Maltohexaose | 31.2 | 41.7 | 17.2 | 15 | 43 |
| Maltoheptaose | 30.3 | 42.6 | 18.9 | 20 | 43.6 |
| Methyl-D-gluco-pyranoside | 29.2 | 1.8 | 11.5 | 13 | 3.8 |
| Palatinose | 31.1 | 13.5 | 9.3 | 9 | 24.8 |
| Panose | 31.1 | 21.2 | 14 | 20 | 37.5 |
| Sophorose | 30.5 | 16.5 | 16.3 | 34 | 33.2 |
| Xylobiose | 28.5 | 10.8 | 20.8 | 22/5 | 16.7/17.3 |
| D-Xylose | 30.7 | 5.9 | 5.7 | 6 | 14.8 |
| L-Xylose | 29.1 | 5.8 | 11 | 15 | 16.0 |

When the AT activity was determined in the radioactivity test, an exchange was also observed with dextrin:

| Oligosaccharide | relative Activity (%) |
|---|---|
| maltose | 100 |
| maltotriose | 27 |
| maltotetraose | 40 |
| maltoheptaose | 49 |
| cellobiose | 15 |
| dextrin | 45 |

5. Modified process for working up acarbose using AT:

In principle, the reaction catalyzed by AT can also be used to enrich acarbose from culture solutions while at the same time converting acarbose homologues into acarbose, in accordance with the following principle:

1) Reacting acarbose or acarbose homologues [acarviosyl-$(G)_n$] with high molecular weight dextrins or starch [$(G)_m$] in the presence of acarviosyl transferase acarviosyl-$(G)_n$+$(G)_m$→acarviosyl-$(G)_m$+$(G)_n$ and removing low molecular weight impurities by dialyzing or precipitating the polysaccharides; and then 2) Reacting with maltose, with the liberation of acarbose, acarviosyl-$(G)_m$+maltose→acarbose+$(G)_m$ The same effect can also be achieved by way of a reactor (e.g. column) using starch and immobilized AT:
- filtering crude acarbose solution through a starch/AT column
- washing to remove impurities
- eluting acarbose with maltose In the above reaction scheme, G represents glucose and m and n in each case represent an integer between 1 and 20, with m and n being different.

6. Culture of E. coli strains, preparation of the plasmid DNA and isolation of DNA fragments E. coli DH5α was incubated at 37° C. in LB medium. Plasmid-harbouring bacteria were maintained under selection pressure (Ampicillin, 100 μg/ml). The cultivation took place on an orbital shaker at 270 rpm. Mixtures which were incubated for at least 16 h were designated overnight cultures (OC).

The cells from 1.5 ml of an OC which had been incubated under selection pressure were employed for preparing plasmid DNA. The plasmids were isolated using the alkaline SDS lysis method (Birnboim and Doly, 1979).

Restriction endonucleases were employed for the specific hydrolysis of vector DNA exclusively in accordance with the manufacturer's instructions (Gibco BRL, Eggenstein, Germany). 5 U of the relevant restriction endonuclease were employed for restricting 10 μg of plasmid DNA, with the incubation being carried out at 37° C. for 2 h. In order to ensure complete hydrolysis, the same quantity of restriction endonuclease was added a second time and the mixture was incubated once again for at least 1 h.

Depending on the sizes of DNA fragments, the cleaved DNA was separated electrophoretically on 0.5–1.2% horizontal agarose gels. For eluting the DNA, the gel piece which contained the DNA fragment was excized with a sterile scalpel and weighed. The DNA fragment was then eluted from the agarose using the JETsorb kit in accordance with the manufacturer's instructions (Genomed, Bad Oeynhausen, Germany).

7. Growth of Actinoplanes sp. SE 50/110, preparation, cleavage of the chromosomal DNA and gel-electrophoretic separation Actinoplanes sp. SE 50/110 was incubated at 30° C. in TSB medium for 3 d on an orbital shaker. While the seed culture (5 ml) was carried out at 240 rpm in small culture tubes, the main culture (50 ml) was carried out at 100 rpm in 500 ml baffled flasks. After the cultivation, the cells were sedimented by centrifugation and washed twice in TE buffer.

The total DNA was prepared by the phenol/chloroform extraction method (Hopwood et al., 1985) using 1.5–2 mg of cells (fresh weight). The 20 μg of chromosomal DNA were hydrolyzed at 37° C. for 2 h with 10 U of the relevant restriction enzyme (Gibco BRL, Eggenstein, Germany) in the appropriate buffer. In order to ensure complete hydrolysis, the same quantity of restriction endonuclease was added a second time and the mixture was incubated once again for at least 1 h.

The cleaved DNA was separated electrophoretically on 0.6% horizontal agarose gels.

The DNA fragments were eluted once again using the JETsorb kit (see Example 6).

8. Preparation of the acb gene probe H

The fragment from pAS2 which was prepared as described in Example 6 was radioactively labelled with the nick-translation system supplied by Gibco BRL, Eggenstein, Germany, in accordance with the latter's instructions. 0.5–1.0 μg of DNA fragment was employed for this purpose. [α$^{32}$P]dCTP was employed (3000 Ci/mM; Amersham, Braunschweig, Germany). The mixture was then boiled for 10 minutes (denaturation) and immediately added to the hybridization solution (see Example 9).

9. Transfer of DNA to membranes, hybridization of DNA (Southern hybridization) and autoradiography DNA fragments were transferred from agarose gels to membranes by the Southern transfer method (Southern, 1975). The agarose gels, which were obtained as described in Example 7, were rinsed for 20 minutes in 0.25 M HCl. The gels were laid on three layers of 3 MM Whatman paper (Whatman, Maidstone, England), and a Hybond™-N+ membrane (Amersham, Braunschweig, Germany) was laid on the gel in such a way that no air bubbles were formed. Several layers of absorbent paper were then laid on the membrane. A weight of approx. 1 kg was then placed on the filter stack. The DNA was transferred by sucking through 0.4M NaOH. After a transfer time of at least 12 h, the nylon filters were rinsed with 2× SSC for 5 minutes and dried in air. The nylon filters were then shaken at 68° C. for at least 2 h in 50–100 ml of prehybridization solution in a water bath. During this period, the solution was changed at least twice. The hybridization was carried out in a hybridization oven for at least 12 h. 15 ml of hybridization solution, containing the acb probe II (see Example 8), were employed.

The nylon filters were subsequently washed for in each case 15 minutes with 6×Postwash and 1×Postwash. The nylon filters were then covered, while still moist, with airtight film. The autoradiography was carried out, at −80° C. for at least 16 h, with Hyperfilm-MP (Amersham, Braunschweig, Germany) in a lightproof cassette using intensifying screens.

10. Isolation and cloning of SstI fragments from the total DNA of Actinoplanes sp. SE 50/110

Actinoplanes sp. chromosomal DNA was completely hydrolyzed with SstI and separated by agarose gel electrophoresis, and the DNA fragments of 9.0 to 12 kb in length were eluted from the agarose (see Example 6). The vector plasmid pUC18 was prepared from E. coli DH5α, hydrolyzed with SstI and treated with alkaline phosphatase (Boehringer, Mannheim, Germany) in accordance with the manufacturer's instructions. The ligation was carried out in a volume of 20 μl, with the ratio of fragment to vector being 3:1, with 0.01–0.1 μg of DNA being present in the mixture. 1 U of the T4 DNA ligase was employed together with the appropriate buffer (Gibco BRL, Eggenstein, Germany).

E. coli DH5α cells which were transformation-competent were transformed with complete ligation mixtures (in accordance with Hanahan, 1983). Ampicillin-resistant transformants were transferred to LB-Amp selection plates (ampicillin, 100 μg/ml).

11. Identification of plasmids which contain the 11 kb SstI fragment from the acarbose biosynthesis cluster Ampicillin-resistant transformants were examined for the presence of the 11 kb SstI fragment which hybridizes with the acb probe II. In each case ten of these clones were streaked out on a selection plate, incubated overnight and washed from the plate with 3 ml of LB medium. The plasmid DNA was then isolated from 20 such pools of ten (using the method of Birnboim and Doly, 1979). In order to remove the cloned SstI fragments from the polylinker, the 20 different plasmid preparations were hydrolyzed with the restriction endonucleases EcoRI and HindIII. The restriction mixtures were then fractionated electrophoretically on a 0.6% agarose gel, and the DNA was transferred from the agarose gel to a nylon filter by means of Southern transfer (see Example 9). Hybridization took place once again using the acb probe II (see Example 9). One of the pools reacted positively with the acb probe II and was divided into the ten individual clones. The plasmids of these clones were likewise isolated and subjected to the above-described method. The plasmid which was hybridized was designated pAS5. It contains a 10.65 kb SstI fragment.

12. Cloning of the 2.6 kb HindIIIPstI fragment

In order to be able to identify additional reading frames, several HindIII/PstI subclones were prepared from plasmid pAS5. For this purpose, plasmid pAS5 was hydrolyzed with the restriction endonucleases HindIII and PstI. The following fragments were obtained:

1.4 kb PstI fragment 5.4 kb PstI fragment 0.05 kb PstI/HindIII fragment 2.6 kb HindIII/PstI fragment 3.8 kb PstI fragment (1.1 kb PstI/SstI fragment ligated to the pUC18 vector)

The resulting DNA fragments were separated by agarose gel electrophoresis and eluted from the gel (see Example 6). The pUC18 vector plasmid was prepared from E. coli DH5α, hydrolyzed with HindIII and PstI and treated with alkaline phosphatase (Boehringer, Mannheim, Germany) in accordance with the manufacturer's instructions. The 2.6 kb HindIII/PstI fragment was cloned. The ligation and transformation were carried out as described in Example 10. The plasmid possessing the 2.6 kb HindIII/PstI fragment was given the designation pAS5/15.1.

13. Amplification and cloning of two 0.3 kb DNA fragments from Actinoplanes sp. chromosomal DNA In order to sequence the overlapping DNA region between the DNA segments cloned in plasmids pAS5/15.5 and pAS5/15.6, two primers (acbD3 and acbD4) were synthesized from the known DNA sequences of these plasmids (see Example 14). Using these primers, a 0.3 kb DNA fragment was amplified from Actinoplanes sp. chromosomal DNA. The denaturing temperature was 95° C. (1 min), the annealing temperature was 68° C. (20 sec), and primer extension took place at 72° C. (20 sec). 25 amplification cycles were carried out. The Taq polymerase was employed in accordance with the manufacturer's directions (Gibco BRL, Eggenstein, Germany). The PCR mixture contained 5% formamide. The BIOMETRA Personal Cycler (Gottingen, Germany) was used for the PCR reaction. The PCR mixture was precipitated with ethanol and the DNA was subsequently ligated into pUC 18 (hydrolyzed with HindIII), and this recombinant plasmid was cloned into E. coli DH5α. In order to sequence the overlapping DNA region between plasmids pAS5/15.4 and pAS5/15.2, a further 0.3 kb DNA fragment was amplified by means of primers acbD5 and acbD6 using the same experimental mixture, and then cloned.

pAS5/15.18 and pAS5/15.19. After the cloning, the PCR fragment which was amplified with primers acbD3 and acbD4 gave rise to the subclone pAS5/15.18, while the PCR fragment which was amplified with primers acbD5 and acbD6 gave rise to the subclone pAS5/15.19.

14. Subcloning fragments from plasmid pAS5

Several fragments were subcloned from plasmid pAS5 in order to elucidate the sequence of the double stranded DNA (FIG. 1).

pAS5/15.1. Plasmid pAS5 was hydrolyzed with the restriction enzymes HindIII and PstI. Five fragments were produced (see Example 12) of which the 2.6 kb HindIII/PstI fragment was cloned. For this purpose, the restriction mixture was separated on a 0.7% agarose gel, and the 2.6 kb HindIII/PstI fragment was eluted from the gel (see Example 6) and ligated into pUC 18 (hydrolyzed with HindIII/PstI), and this recombinant plasmid was cloned into *E. coli* DH5α.

pAS5/15.2; pAS5/15.3; pAS5/15.4; pAS5/15.5. Plasmid pAS5/15.1 was hydrolyzed with the restriction enzyme SalI. The resulting 6 fragments were separated on a 1% agarose gel. The fragments had the following sizes: 0.75 kb, 0.5 kb, 0.4 kb, 0.35 kb, 0.05 kb and 3.2 kb (0.5 kb fragment ligated to pUC18). The fragments which were earmarked for the subcloning were eluted from the gel (see Example 6). The pUC18 vector was prepared for the cloning using the restriction enzyme SalI as described in Example 6. The ligations were carried out as described in Example 10. The 0.75 kb fragment was ligated into the prepared pUC 18, resulting in plasmid pAS5/15.2. Plasmid pAS5/15.3 was obtained after ligating the 0.5 kb fragment to the prepared pUC18. Plasmid pAS5/15.4 contains the 0.4 kb fragment, and the 0.35 kb fragment is a component of plasmid pAS5/15.5.

pAS5/15.6; pAS5/15.7; pAS5/15.9. Plasmid pAS5/15.1 was hydrolyzed with the restriction enzyme PvuII. The 5 fragments which resulted were separated on a 1.2% agarose gel. The fragments had the following sizes:

1.25 kb PvuII fragment 0.15 kb PvuII fragment 0.8 kb PvuII fragment (0.7 kb PvyII/HindIII fragment ligated to 0.1 kb HindIII/PvuII fragment from pUC18)

0.66 kb PvuII fragment (0.5 kb PvuII/PstI fragment ligated to 0.16 kb PstI/PvuII fragment from pUC 18)

2.4 kb PvuII fragment (the residue of the pUC 18 vector)

The 1.25 kb fragment was ligated into pUC18 (hydrolyzed with HincII), and this recombinant plasmid was cloned in *E. coli* DH5α, giving rise to plasmid pAS5/15.6. Plasmid pAS5/15.7 was obtained after cloning the 0.8 kb fragment into the HincII-hydrolyzed pUC18 vector plasmid. Plasmid pAS5/15.9 contains the 0.15 kb fragment. pAS5/15.12. Plasmid pAS5/15.1 was hydrolyzed with the restriction endonucleases NcoI and KpnI. The resulting 0.9 kb NcoI/KpnI fragment was eluted from a 1.2% agarose gel (see Example 6) and ligated into the vector pUCBM21 (hydrolyzed with NcoI/KpnI), and this recombinant vector was cloned in *E. coli* DH5α; this resulted in plasmid pAS5/15.12.

15. DNA sequencing of the Actinoplanes sp. 2.6 kb HindIII/PstI fragment

The plasmids described in Examples 13 and 14 were sequenced. 6–8 μg of plasmid DNA from one preparation (see Example 6) were employed in the sequencing reaction. The sequencing reaction was carried out using the Auto-Read Sequencing kit (Pharmacia, Freiburg, Germany). The standard protocol for sequencing dsDNA was used. In order to make it possible to evaluate the nucleotide sequence using the A.L.F., the fluorescein-labelled universal and reverse sequencing primers were used as the starting molecules for the sequencing reaction (see Tab. 3). For preparing the gel, 8 ml of Hydro Link Long Ranger (Serva, Heidelberg, Germany), 33.6 g of urea, 8 ml of 10× TBE buffer and $H_2O$ to 80 ml were mixed, and the mixture was sterilized by filtration and degassed for 1 minute. Polymerization was initiated by adding 350 μl of 10% (w/v) ammonium persulphate and 40 μl of N,N,N',N'-tetramethylethylenediamine. The solution was poured into a gel form (50×50×0.05 cm). The electrophoresis was carried out at 38 W at a constant temperature of 45° C. 1× TBE buffer was used as the running buffer. The measured fluorescence was processed into a DNA sequence using a linked-in computer (Compaq 386/20e), which was also used to control the electrophoresis unit (A.L.F. Manager 2.5 program; Pharmacia).

16. Overexpression of acarviosyl transferase in *S. lividans*

Figure 2:
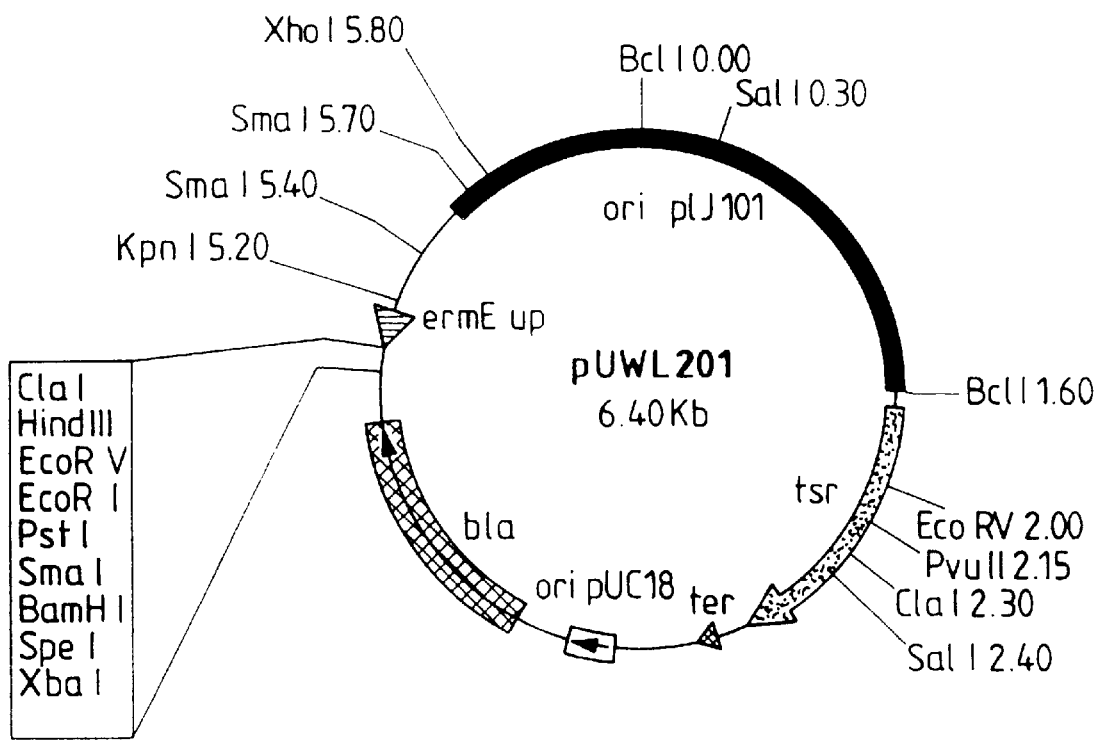
FIG. 2 Structure of the expression vector pUWL201.

The gene for Actinoplanes sp. acarviosyl transferase (acbD) was expressed in *Streptomyces lividans* TK21 from the shuttle vector pUWL201 (U. Wehmeier, unpublished, FIG. 2). The plasmid (6.4 kb) is composed of the vector pUWL199 (Wehmeier, 1995) in which the 2.0 kb KpnI/XbaI fragment is replaced by a KpnI/XbaI fragment consisting of the ermE*p promoter (Bipp et al., 1994) and the HincII/ClaI moiety of the pBLUESCRIPT multilinker (Stratagene). For cloning the acbD gene in *E. coli* DH5α and *Streptomyces lividans* TK21, plasmid pAS5/15.1 (see Example 12) was hydrolyzed with the restriction endonucleases HindIII and PstI. The resulting 2.6 kb HindIII/PstI fragment was ligated into vector pUWL201 (hydrolyzed with HindIII and PstI), and the resulting recombinant plasmid was cloned in *E. coli* DH5α. The resulting plasmid was given the designation pAS9. Plasmid pAS9 was prepared from *E. coli* DH5α by alkaline lysis and cloned into *S. lividans* TK21 using the protoplast transformation method (Hopwood et al., 1985). In this clone, the acbD gene is under the control of the constitutive ermE*p promoter (M. Bibb, Norwich, England; personal communication). After *S. lividans* TK21/pAS9 had been cultured in TSB medium (25 μg/ml thiostreptone), it was possible to detect an additional protein in the supernatant as a significant band of 75 kDa on an SDS polyacrylamide gel (Lugtenberg et al., 1975).

17. Inactivation of the acarviosyl transferase by means of gene disruption

The Actinoplanes sp. acarviosyl transferase gene (acbD) was inactivated by the method of gene disruption. For this purpose, the chromosomal acbD gene in Actinoplanes sp. was partially replaced by an antibiotic resistance gene. The antibiotic resistance genes were inserted by homologous recombination. It was demonstrated in preliminary experiments that Actinoplanes sp. was sensitive to the antiobiotics erythromycin, streptomycin, apramycin, neomycin and kanamycin. The antibiotic resistance genes ermE, aphD1, aaC4 and aph were therefore employed for the mutagenesis. In a first example, the gene for resistance to erythromycin (ermE) from the vector pUGTI (Ingham et al., 1995) was used for inactivating acbD. For this, the resistance gene, on a 1.5 kb-sized KpnI fragment, was separated on an agarose gel, after having hydrolyzed pUGTI with KpnI, and then isolated from the gel. Plasmid pAS5/15.1 (see Example 12) was linearized with the restriction endonuclease NcoI. The NcoI recognition sequence is at 1050 bp on the 2.6 kb cloned chromosomal fragment. The hydrolyzed ends of plasmid pAS5/15.1 and of the prepared 1.5 kb KpnI fragment were converted into smooth DNA double-stranded ends with the Klenow fragment of DNA polymerase I in accordance with the producer's instructions (Gibco BRL, Eggenstein, Germany). By means of the subsequent ligation, the erythromycin resistance gene, which is present on the 1.5 kb KpnI fragment, was cloned into the acbD gene on plasmid pAS5/15.1 in *E. coli* DH5α. This plasmid was linearized and introduced using customary methods (protoplast transformation). The recombinant plasmid can also be transferred by conjugation with *E. coli* S17-1 and Actinoplanes sp. The method of electroporation constitutes an additional option for plasmid transfer. The chromosomal acbD gene was replaced by the erythromycin resistance gene-interrupted acbD gene of the constructed plasmid as a result of homologous recombination. Due to a double crossover having taken place, an erythromycin-resistant, acbD mutant of Actinoplanes sp. SE 50/110 was produced. The following methods can also be employed for recombining alternative resistance genes into Actinoplanes sp.: (1) electroporation, (2) protoplast transformation (Hopwood et al., 1985), (3) mycelial transformation (Madon and Hutter, 1991) and (4) conjugation (Mazodier et al., 1989).

Buffers and solutions:
Media for growing bacteria
LB medium:

| tryptone | 10 g |
| NaCl | 10 g |
| yeast extract | 5 g |
| $H_2O$ | to 1000 ml |

The pH was adjusted to 7.5 with 4M NaOH
TSB medium:
   tryptone-soya broth (oxoid) 30 g

| $H_2O$ | to 1000 ml |

TE buffer (pH 8.0)

| Tris-HCl | 10 mM |
| $Na_2$-EDTA | 1 mM |

Standard preparation of plasmid DNA
(modified from Birnboim and Doly, 1979)

| Mix I | 50 mM glucose |
| | 50 mM Tris-HCl (pH 8.0) |
| | 10 mM EDTA (pH 8.0) |
| | 5 mg of lysozyme/ml |
| Mix II | 200 ml of NaOH |
| | 1% (w/v) SDS (sodium dodecyl sulphate) |
| Mix III | 3 M potassium acetate |
| | 1.8 M formate |

DNA/DNA hybridization

| 20x SSC | 3 M NaCl |
| | 0.3 M Na citrate | prehybridization solution:
6x SSC
0.01 M sodium phosphate buffer, pH 6.8
1 mM EDTA
0.5% SDS
0.1% skimmed milk powder
hybridization solution:
   The acb probe is added, after the labelling reaction, to 15 ml of prehybridization solution.

6xPostwash
   6x SSC
   0.5% SDS
DNA sequencing
   TBE buffer (pH 8.0)
      1 M Tris base
      0.83 M boric acid
      10 mM EDTA

LITERATURE

1) Bibb, M. J. et al. (1994)
   The mRNA for the 23 S rRNA methylase encoded by the ermE gene of *Saccharopolyspora erythraea* is translated in the absence of a conventional ribosome-binding site
   Mol. Microbiol. 14, 533–545.
2) Birnboim, H. C., J. Doly (1979)
   A rapid alkaline extraction procedure for screening recombinant plasmid DNA
   Nucleic Acids Res. 7, 1513–1523
3) Hanahan, D. (1983)
   Studies on transformation of Escherichia coli with plasmids
   J. Mol. Biol. 166, 557–580
4) Hopwood, D. A. et al. (1985)
   Genetic manipulation of Streptomyces;
   A laboratory manual; The John Innes Foundation, Norwich, England
5) Ingham, C. J., et al. (1995)
   Rho-independent terminators without 3'poly-U tails from the early region of actinophage phi C31
   Nucleic Acids Res. 23, 370–373.
6) Lugtenberg, B. et al. (1975)
   Electrophoretic resolution of the major outer membrane protein of *Escherichia coli* into four bands
   FEBS Lett. 58, 254–258.
7) Madon, J., R. Hütter (1991)
   Transformation System for *Amycolatopsis* (*Nocardia*) *mediterranei*; direct transformation of mycelium with plasmid DNA.
   J. Bacteriol. 173, 6325–6331
8) Mazodier, P. et al. (1989)
   Intergenic conjugation between *Escherichia coli* and Streptomyces species
   J. Bacteriol. 171, 3583–3585
9) Sanger, F. et al. (1977)
   DNA sequencing with chain terminating inhibitors
   Proc. Natl. Acad. Sci. USA 74, 5463–5467
10) Southern, E. M. (1975)
   Detection of specific sequences among DNA fragments separated by gel electrophoresis
   J. Mol. Biol. 98, 503–521
11) Wehmeier, U. F. (1995)
   New functional Escherichia coli-Streptomyces shuttle vectors allowing blue-white screening on Xgal plates
   Gene 165, 149–150

We claim:

1. An isolated DNA sequence encoding the amino acid sequence of SEQ ID NO.: 1 or a fragment of said DNA sequence encoding an acarviosyl transferase.

2. An isolated DNA sequence according to claim 1, which comprises the nucleotide sequence of SEQ ID NO.: 2.

3. A vector comprising a DNA sequence according to claim 1.

4. A vector comprising a DNA sequence according to claim 2.

5. A method for preparing acarviosyl transferase comprising expressing a vector according to claim 3 in a heterologous host organism and recovering acarviosyl transferase.

6. A method for preparing acarviosyl transferase comprising expressing a vector according to claim 4 in a heterologous host organism and recovering acarviosyl transferase.

7. An isolated DNA sequence which encodes acarviosyl transferase and hybridizes to a DNA sequence encoding the amino add sequence of SEQ ID NO.: 1 under the following conditions:
   a) prehybridization at 68° C. for at least 2 hours in 50–100 ml of prehybridization solution in a water bath; followed by
   b) hybridization in a hybridization oven for at least 12 hours; followed by
   c) washing for 15 minutes each with 6×postwash and 1×postwash.

8. A vector comprising a DNA sequence according to claim 7.

9. A method for preparing acarviosyl transferase comprising expressing a vector according to claim 8 in a heterologous host organism and recovering acarviosyl transferase.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
            (A) LENGTH: 725 amino acids
            (B) TYPE: amino acid
            (D) TOPOLOGY: linear (xi) SEQUENCE DESCRIPTION: SEQ ID NO: 1:

Val Gln Arg His Ala Arg His Ala Ile Ala
1               5                   10

Ala Ala Val Gly Phe Pro Leu Leu Pro Pro
                15                  20

Ser Leu Pro Ala His Ala Ala Gly Ala Ser
                25                  30

Ala Val Val Pro Tyr Ala Gly Asn Pro Ala
                35                  40

Ser Leu Lys Gln Asp Leu Cys Tyr Gln Ile
                45                  50

Ala Thr Asp Arg Phe Ser Asp Gly Thr Pro
                55                  60

Ala Asn Asn Asn Pro Gly Asn Val Pro Gly
                65                  70

Met Phe Ala Asp Lys Thr Lys Leu Asn Asp
                75                  80

Arg Gln Glu Trp Leu Lys Tyr Met Gly Gly
                85                  90

Asp Phe Ala Gly Ile Thr Gln Arg Met Glu
                95                  100

Tyr Leu Lys Asn Leu Gly Val Gly Ala Ile
                105                 110

Trp Ile Ser Pro His Val Asp Asn Ile Asn
                115                 120

Val Pro Ala Asn Gly Ala Thr Gly Tyr His
                125                 130

Gly Tyr Trp Pro Arg Asp Phe Lys Arg Leu
                135                 140

Glu Glu His Phe Gly Thr Asp Glu Glu Phe
                145                 150

Asp Ala Leu Val Ser Ala Ala His Ala Ser
                155                 160

Asn Ile Lys Val Ile Met Asp Trp Thr Pro
                165                 170

Asn Gly Thr Asn Pro Pro Asn Gln Ala Glu
                175                 180

Asp Gly Ala Leu Tyr Asp Asp Gly Gln Leu
                185                 190

Val Gly Arg Tyr Gly Ala Asp Ser Ala Gly
                195                 200

His Phe His His Gly Pro Ala Ile Gly Asp
                205                 210

Phe Asn Asp Arg Tyr Gln Asp Gln Tyr Tyr
                215                 220

Ser Leu Ala Asp Ile Ala Asp Leu Asp Gln
                225                 230

Gln Asn Pro Arg Val Asp Gln Leu Leu Lys
                235                 240

Asp Asp Ala Asn Tyr Trp Met Asp Arg Gly

```
                        245                 250
Val Asp Gly Ile Arg Val Asp Ala Val Lys
                255                 260

His Met Pro Leu Ser Trp Gln Arg Ser Phe
                265                 270

Ala Asp Ala Val Thr Ser His Lys Ser Ala
                275                 280

Ala Ile Phe Gly Glu Trp Tyr Met Gly Asp
                285                 290

Gln Ser Asp Pro Leu Tyr Ala Asp Gln Val
                295                 300

Lys Phe Ala Asn Thr Ser Gly Ile Ala Ala
                305                 310

Met Asp Phe Tyr Thr Asn Arg Ser Ile Arg
                315                 320

Asp Thr Phe Ala Gly Ala Gly Ser Met Lys
                325                 330

Ser Leu Asp Ala Ala Ile Thr Lys Thr Asn
                335                 340

Arg Asp Tyr Leu Tyr Glu Gln Asp Leu Ile
                345                 350

Thr Phe Leu Asp Asn Gln Asp Thr Arg Arg
                355                 360

Phe Gly Thr Leu Asn Ser Asp Pro Ala Ala
                365                 370

Leu His Arg Ala Leu Ala Phe Leu Leu Thr
                375                 380

Thr Arg Gly Thr Pro Cys Leu Phe Tyr Gly
                385                 390

Thr Glu Gln Tyr Leu His Asn Asp Thr Gly
                395                 400

Glu Gly Ser Asn Lys Gly Lys Asp Pro Tyr
                405                 410

Asn Arg Pro Pro Met Ala Ser Phe Asp Thr
                415                 420

Asp Thr Val Ala Tyr Arg Glu Ile Arg Arg
                425                 430

Pro Leu Arg Pro Ala Pro Val Glu Pro Arg
                435                 440

Gly Gly Tyr Gly Asp His Gln Gln Arg Trp
                445                 450

Ile Asn Asp Asp Val Tyr Val Tyr Glu Arg
                455                 460

Arg Phe Gly Asp Asn Val Leu Leu Thr Ala
                465                 470

Ile Asn Lys Gly Ser His Glu Tyr Arg Leu
                475                 480

Glu Arg Ala Gly Thr Ala Leu Pro Ala Gly
                485                 490

Thr Tyr Arg Asp Val Leu Gly Gly Thr Phe
                495                 500

Gly Gly Ser Asp Leu Thr Val Glu Asp Gly
                505                 510
```

Asp Gly Thr Asp Arg Ser Thr Val Ala Pro
            515                 520

Val Leu Gly Ala Gly Gln Val Ala Val Trp
            525                 530

Ser Tyr Arg Ala Pro Val Asp Thr Glu Pro
            535                 540

Arg Ile Gly Gly Val Gly Pro Val Val Thr
            545                 550

Arg Ala Gly Ala Thr Val Thr Val Glu Gly
            555                 560

Thr Gly Phe Gly Ser Gly Gly Thr Val Ala
            565                 570

Ile Gly Gly Val Pro Ala Thr Val Gln Gln
            575                 580

Trp Thr Ala Asp Arg Ile Thr Ala Thr Val
            585                 590

Pro Val Gly Val Pro Thr Gly Ala Val Gln
            595                 600

Val Thr Val Gly Asn Gly Ser Gly Thr Ser
            605                 610

Asn Gly Tyr Pro Ile Thr Thr Arg Thr Gly
            615                 620

Lys Pro Val Pro Val Gln Phe Thr Val Gln
            625                 630

Asn Pro Pro Ala Thr Ala Pro Gly Glu Ser
            635                 640

Leu Tyr Leu Thr Gly Asp Val Ala Glu Leu
            645                 650

Gly His Trp Ser Thr Ser Pro Asp Gln Thr
            655                 660

Ala Gly Gln Leu Leu Arg Val Pro Asn Glu
            665                 670

Ser Arg Gly Val Leu Val Ala Asp Leu Pro
            675                 680

Ala Gly Ala Pro Val Glu Phe Lys Phe Val
            685                 690

Lys Val Ala Ala Asp Gly Thr Val Thr Trp
            695                 700

Glu Gly Gly Ala Asn His Arg Tyr Thr Val
            705                 710

Pro Ala Gly Gly Thr Gly Thr Thr Ser Leu
            715                 720

Thr Trp Gln Arg Glx
            725

(2) INFORMATION FOR SEQ ID NO: 2:

(i) SEQUENCE CHARACTERISTICS:
        (A) LENGTH: 2582 nucleotides
        (B) TYPE: nucleic acid
        (C) STRANDEDNESS: double
        (D) TOPOLOGY: linear (xi) SEQUENCE DESCRIPTION: SEQ ID NO: 2:

AAGCTTGAAG TGGCGGTGAT GCATCCATCA CTGTATGCGC                                40

ATCTGAATGA CGTCTTCTGC AAGTTCTTGC AGCGGTCTCC                                80

-continued

```
GGGCCCTGCC CTTCCTCGTC ATCCCTTCAC AAGGAGAAGC         120
TCGTGCAACG TCACGCCAGG CATGCCATCG CCGCGGCGGT         160
AGGCTTTCCG CTGCTGCCGC CGTCACTGCC GGCTCATGCC         200
GCCGGGGCTT CGGCCGTGGT GCCGTACGCC GGTAACCCGG         240
CCAGTCTCAA GCAGGACCTC TGCTACCAGA TCGCCACCGA         280
CCGGTTCAGC GACGGGACCC CGGCGAACAA CAATCCGGGC         320
AACGTGCCCG GCATGTTCGC CGACAAGACC AAGCTGAACG         360
ACCGGCAGGA GTGGCTCAAA TACATGGGAG GTGACTTCGC         400
CGGCATCACC CAGCGGATGG AGTACCTCAA GAACCTGGGC         440
GTCGGCGCGA TCTGGATCTC GCCGCACGTC GACAACATCA         480
ACGTTCCGGC GAACGGCGCC ACCGGTTACC ACGGCTACTG         520
GCCGCGCGAC TTCAAGCGGC TCGAAGAGCA CTTCGGCACC         560
GACGAGGAGT TCGACGCGCT GGTGTCGGCG GCGCACGCCA         600
GCAACATCAA AGTGATCATG GACTGGACGC CGAACGGCAC         640
CAACCCGCCG AACCAGGCCG AGGACGGCGC CCTCTACGAC         680
GATGGGCAGC TGGTCGGCAG GTACGGGCG GACAGTGCCG          720
GGCACTTCCA CCACGGCCCG GCGATCGGCG ACTTCAACGA         760
TCGCTACCAG GACCAGTACT ACAGCCTGGC CGACATCGCC         800
GACCTCGACC AGCAGAACCC GCGGGTCGAC CAGCTGCTCA         840
AGGACGACGC CAACTACTGG ATGGACCGCG GGTCGACGG          880
CATCCGGGTC GACGCCGTCA AGCACATGCC GCTGAGCTGG         920
CAGCGGTCCT TCGCCGACGC GGTCACCTCG CACAAGAGCG         960
CGGCCATCTT CGGCGAGTGG TACATGGGCG ACCAGTCCGA         1000
TCCGCTCTAC GCCGACCAGG TCAAGTTCGC CAACACCAGC         1040
GGCATCGCGG CCATGGACTT CTACACCAAC CGCTCGATCC         1080
GCGACACCTT CGCCGGCGCC GGCTCGATGA AGTCCCTGGA         1120
CGCGGCGATC ACCAAGACCA ACCGGGACTA CCTCTACGAG         1160
CAGGATCTGA TCACGTTCCT GGACAACCAG GACACCCGGC         1200
GCTTCGGGAC GCTCAACAGC GATCCGGCGG CCCTGCACCG         1240
GGCGCTCGCC TTCCTGCTCA CCACCCGGGG TACGCCGTGC         1280
CTGTTCTACG GCACCGAGCA GTACCTGCAC AACGACACCG         1320
GTGAGGGCAG CAACAAGGGC AAGGACCCGT ACAACCGGCC         1360
CCCGATGGCC AGTTTCGACA CCGACACGGT CGCCTACCGG         1400
GAGATCCGGC GCCCTCTCCG ACCTGCGCCG GTCGAACCCC         1440
GCGGTGGCTA CGGGGACCAC CAGCAGCGGT GGATCAACGA         1480
CGACGTGTAC GTCTACGAGC GCCGGTTCGG CGACAACGTG         1520
CTGCTGACCG CCATCAACAA GGGCTCGCAC GAGTACCGGC         1560
TCGAACGGGC TGGCACCGCG CTGCCGGCCG GCACCTATCG         1600
CGACGTGCTC GGCGGCACCT TCGGCGGCTC CGACCTGACC         1640
GTCGAGGACG GCGACGGCAC CGACCGGTCG ACCGTCGCGC         1680
```

| | |
|---|---|
| CGGTGCTGGG TGCCGGGCAG GTCGCCGTCT GGTCGTACCG | 1720 |
| GGCGCCGGTG GACACCGAGC CCCGGATCGG CGGGGTCGGG | 1760 |
| CCGGTCGTGA CCCGGGCCGG CGCCACCGTC ACCGTCGAGG | 1800 |
| GCACCGGCTT CGGCTCCGGC GGAACCGTCG CGATCGGCGG | 1840 |
| AGTCCCCGCG ACCGTCCAGC AGTGGACGGC GGACCGTATC | 1880 |
| ACCGCCACCG TCCCGGTCGG CGTTCCCACC GGGGCCGTCC | 1920 |
| AGGTGACCGT CGGCAACGGC TCCGGCACCA GCAACGGGTA | 1960 |
| CCCGATCACC ACCCGTACCG GAAAACCGGT CCCGGTGCAG | 2000 |
| TTCACCGTTC AGAACCCGCC GGCCACCGCG CCCGGGGAGT | 2040 |
| CGCTCTACCT GACCGGTGAC GTCGCCGAGT TGGGGCACTG | 2080 |
| GTCGACCAGC CCGGACCAGA CCGCGGGACA GCTGCTGCGG | 2120 |
| GTGCCGAACG AGTCCCGGGG CGTCCTCGTC GCCGACCTGC | 2160 |
| CGGCCGGGGC GCCGGTCGAG TTCAAGTTCG TCAAGGTCGC | 2200 |
| GGCCGACGGC ACGGTGACCT GGGAGGGTGG TGCCAACCAC | 2240 |
| CGGTACACCG TCCCGGCCGG CGGCACCGGC ACGACCAGCC | 2280 |
| TCACCTGGCA GCGCTGACGC CACCGTGCGG AGGGCCCGGC | 2320 |
| CGTGACCGGG CCCGCCGCAC CGGGCCGGGC GGTGGAACGG | 2360 |
| CCGGGACGGT TGGGCGCCGG CCCCGGCGTG GCGAGATCGA | 2400 |
| GGGCTGCGCA CACCGGGGGC TTGAACGGCT GGTCTGGCCC | 2440 |
| CAAGGCGACG GTTCCCGTCG GCGAGTATCT CACCTTCAAG | 2480 |
| GGTCCCCGGA CGCCTCGCCC GGCTTCTCCA CCAGCGCCGA | 2520 |
| CGGTTACCAG ATCACCCCTT GGTGGAGCCG AGGGAGAGGC | 2560 |
| CGGCGATGAA CTGCTTCTGC AG | 2582 |

(2) INFORMATION FOR SEQ ID NO: 3:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 3:

| | |
|---|---|
| ACCAGGCCGA GGACGGCGCC C | 21 |

(2) INFORMATION FOR SEQ ID NO: 4:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 4:

| | |
|---|---|
| AGCGGCATGT GCTTGACGGC G | 21 |

(2) INFORMATION FOR SEQ ID NO: 5:

(i) SEQUENCE CHARACTERISTICS:
        (A) LENGTH: 23 nucleotides
        (B) TYPE: nucleic acid
        (C) STRANDEDNESS: single (D) TOPOLOGY: linear (xi) SEQUENCE DESCRIPTION: SEQ ID NO: 5:

ACCGGCTCGA ACGGGCTGGC ACC                                        23

(2) INFORMATION FOR SEQ ID NO: 6:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 6:

CCCTCGACGG TGACGGTGGC G                                          21

(2) INFORMATION FOR SEQ ID NO: 7:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 7:

GTAAAACGAC GGCCAGT                                               17

(2) INFORMATION FOR SEQ ID NO: 8:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (xi) SEQUENCE DESCRIPTION: SEQ ID NO: 8:

GAAACAGCTA TGACCATG                                              18

(2) INFORMATION FOR SEQ ID NO: 9:

(i) SEQUENCE CHARACTERISTICS:
        (A) LENGTH: 23 amino acids
        (B) TYPE: amino acid
        (D) TOPOLOGY: linear (xi) SEQUENCE DESCRIPTION: SEQ ID NO: 9:

Asn Leu Gly Val Gly Ala Ile Trp Ile Ser Pro His
 1               5                  10

Val Asp Asn Ile Asn Val Pro Ala Ala Gly Gly
                15                  20

(2) INFORMATION FOR SEQ ID NO: 10:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO: 10:

Thr Gly Lys Pro Val Pro Val Gln Phe Thr Val Gln
 1               5                  10

Asn Pro Pro Ala Thr Ala Pro Gly Glu
                15                  20

(2) INFORMATION FOR SEQ ID NO: 11:

```
       (i) SEQUENCE CHARACTERISTICS:
            (A) LENGTH: 18 amino acids
            (B) TYPE: amino acid
            (D) TOPOLOGY: linear (xi) SEQUENCE DESCRIPTION: SEQ ID NO: 11:

Ser Thr Val Ala Pro Val Leu Gly Ala Gly Gln Val
1               5                   10
Ala Val Trp Ser Tyr Arg
            15

(2) INFORMATION FOR SEQ ID NO: 12:

(i) SEQUENCE CHARACTERISTICS:
            (A) LENGTH: 20 amino acids
            (B) TYPE: amino acid
            (D) TOPOLOGY: linear (xi) SEQUENCE DESCRIPTION: SEQ ID NO: 12:

Tyr Gln Asp Gln Tyr Tyr Ser Leu Ala Asp Ile Ala
1               5                   10
Asp Leu Asp Gln Gln Asn Pro Arg
            15                  20

(2) INFORMATION FOR SEQ ID NO: 13:

(i) SEQUENCE CHARACTERISTICS:
            (A) LENGTH: 12 amino acids
            (B) TYPE: amino acid
            (D) TOPOLOGY: linear (xi) SEQUENCE DESCRIPTION: SEQ ID NO: 13:

Trp Ile Asn Asp Asp Val Tyr Val Tyr Glu Arg Leu
1               5                   10

(2) INFORMATION FOR SEQ ID NO: 14:

(i) SEQUENCE CHARACTERISTICS:
            (A) LENGTH: 18 amino acids
            (B) TYPE: amino acid
            (D) TOPOLOGY: linear (xi) SEQUENCE DESCRIPTION: SEQ ID NO: 14:

Asp Tyr Leu Tyr Glu Gln Asp Leu Ile Thr Phe Leu
1               5                   10
Asp Asn Gln Asp Thr Arg
            15

(2) INFORMATION FOR SEQ ID NO: 15:

(i) SEQUENCE CHARACTERISTICS:
            (A) LENGTH: 9 amino acids
            (B) TYPE: amino acid
            (D) TOPOLOGY: linear (xi) SEQUENCE DESCRIPTION: SEQ ID NO: 15:

Asp Asp Ala Asn Tyr Trp Met Asp Arg
1               5

(2) INFORMATION FOR SEQ ID NO: 16:

(i) SEQUENCE CHARACTERISTICS:
            (A) LENGTH: 12 amino acids
            (B) TYPE: amino acid
            (D) TOPOLOGY: linear
```

(xi) SEQUENCE DESCRIPTION: SEQ ID NO: 16:

Ala Val Leu Thr Gly Asn Thr Val Tyr Asp Trp Lys
1               5                   10